(12) United States Patent
Fletcher et al.

(10) Patent No.: US 12,377,393 B2
(45) Date of Patent: Aug. 5, 2025

(54) AUTOMATED METHOD AND APPARATUS FOR PREPARING BIOPROCESS SOLUTIONS

(71) Applicant: FUJIFILM Irvine Scientific, Inc., Santa Ana, CA (US)

(72) Inventors: Thomas Reid Fletcher, Newport Beach, CA (US); David Neese, Escondido, CA (US); Wayne Mauro, Lake Forest, CA (US)

(73) Assignee: FUJIFILM Irvine Scientific, Inc., Santa Ana, CA (US)

( * ) Notice: Subject to any disclaimer, the term of this patent is extended or adjusted under 35 U.S.C. 154(b) by 0 days.

(21) Appl. No.: 18/438,196

(22) Filed: Feb. 9, 2024

(65) Prior Publication Data

US 2024/0181409 A1 Jun. 6, 2024

Related U.S. Application Data

(62) Division of application No. 17/398,829, filed on Aug. 10, 2021, now Pat. No. 11,925,913, which is a
(Continued)

(51) Int. Cl.
*C12M 1/02* (2006.01)
*B01F 21/00* (2022.01)
(Continued)

(52) U.S. Cl.
CPC ........ *B01F 35/21112* (2022.01); *B01F 21/30* (2022.01); *B01F 23/49* (2022.01);
(Continued)

(58) Field of Classification Search
CPC .............................. C12M 41/40; C12M 41/44
(Continued)

(56) References Cited

U.S. PATENT DOCUMENTS 266,081 A    10/1882   Berry
342,998 A     6/1886   Berry
(Continued)

FOREIGN PATENT DOCUMENTS

CN          104212704       12/2014
DE           29813996 U1    10/1998
(Continued)

OTHER PUBLICATIONS

Examination Report No. 1 dated May 18, 2023 issued in AU Application No. 2018292271, 3 pages.
(Continued)

*Primary Examiner* — David L Sorkin
(74) *Attorney, Agent, or Firm* — FOLEY & LARDNER LLP

(57) ABSTRACT

An automated bioprocess solution preparation apparatus includes a first mixing chamber containing at least one ingredient for a bioprocess solution, a first port and a second port for a fluid to enter the mixing chamber, and a third port for a liquid bioprocess solution to exit the mixing chamber. The apparatus further includes an array of tubing for fluid flow within the apparatus, a sensor arranged to measure a property of the liquid bioprocess solution exiting the mixing chamber, a first valve associated with the first port, and a second valve associated with the second port. When the property meets or exceeds a threshold value, the apparatus is operable to perform at least one of: closing the first valve to block the fluid from entering the mixing chamber through the first port, and opening the second valve for the fluid to enter the mixing chamber through the second port.

20 Claims, 11 Drawing Sheets

Related U.S. Application Data division of application No. 16/017,014, filed on Jun. 25, 2018, now Pat. No. 11,097,237.

(60) Provisional application No. 62/527,878, filed on Jun. 30, 2017.

(51) Int. Cl.
| | |
|---|---|
| *B01F 23/40* | (2022.01) |
| *B01F 23/80* | (2022.01) |
| *B01F 25/10* | (2022.01) |
| *B01F 25/316* | (2022.01) |
| *B01F 33/81* | (2022.01) |
| *B01F 35/21* | (2022.01) |
| *C12M 1/00* | (2006.01) |
| *C12M 1/33* | (2006.01) |
| *C12M 1/34* | (2006.01) |

(52) U.S. Cl.
CPC .......... *B01F 23/808* (2022.01); *B01F 25/101* (2022.01); *B01F 25/102* (2022.01); *B01F 25/316* (2022.01); *B01F 33/811* (2022.01); *B01F 35/2111* (2022.01); *B01F 35/2113* (2022.01); *B01F 35/2132* (2022.01); *B01F 35/2133* (2022.01); *C12M 27/00* (2013.01); *C12M 41/26* (2013.01); *C12M 45/02* (2013.01); *C12M 99/00* (2013.01)

(58) Field of Classification Search
USPC ..... 366/152.1–152.4; 137/4, 5, 7, 88, 92, 93
See application file for complete search history.

(56) References Cited

U.S. PATENT DOCUMENTS

| | | | | |
|---|---|---|---|---|
| 1,992,581 | A | * | 2/1935 | Reeder ................. G05D 23/132 210/453 |
| 2,451,715 | A | | 10/1948 | Caldwell |
| 2,636,812 | A | | 4/1953 | Atkinson |
| 3,109,631 | A | * | 11/1963 | Purjahn ................. B01F 25/313 366/152.2 |
| 3,261,593 | A | | 7/1966 | Sharples |
| 3,383,178 | A | | 5/1968 | Dietz |
| 3,468,633 | A | | 9/1969 | Honchar |
| 5,232,848 | A | | 8/1993 | Wolfe et al. |
| 5,470,151 | A | | 11/1995 | Walthall et al. |
| 5,641,410 | A | * | 6/1997 | Peltzer ................. B01J 19/0006 137/5 |
| 6,065,860 | A | | 5/2000 | Fuchsbichler |
| 6,120,175 | A | * | 9/2000 | Tewell ................. B01F 35/881 366/177.1 |
| 6,186,657 | B1 | | 2/2001 | Fuchsbichler |
| 6,224,778 | B1 | * | 5/2001 | Peltzer .................... C02F 1/008 210/101 |
| 6,588,929 | B1 | | 7/2003 | Dornbush |
| 6,609,857 | B1 | | 8/2003 | Hjortstam et al. |
| 6,967,002 | B1 | | 11/2005 | Edgson et al. |
| 7,448,790 | B2 | | 11/2008 | Tessien et al. |
| 8,382,364 | B2 | | 2/2013 | Hildreth |
| 10,150,941 | B2 | | 12/2018 | Fletcher |
| 2002/0048213 | A1 | * | 4/2002 | Wilmer ............... B01F 35/2134 366/136 |
| 2004/0057334 | A1 | * | 3/2004 | Wilmer ............... B01F 25/4335 366/136 |
| 2006/0252145 | A1 | | 11/2006 | House et al. |
| 2009/0061518 | A1 | | 3/2009 | House et al. |
| 2010/0008180 | A1 | | 1/2010 | Krogh |
| 2012/0156783 | A1 | | 6/2012 | Kubiak et al. |
| 2013/0102071 | A1 | | 4/2013 | Pan et al. |
| 2015/0124554 | A1 | * | 5/2015 | Haden ................... B01F 23/451 366/165.1 |
| 2017/0058244 | A1 | | 3/2017 | Labarge et al. |
| 2017/0145368 | A1 | | 5/2017 | Fletcher |

FOREIGN PATENT DOCUMENTS

| | | |
|---|---|---|
| JP | S52-029673 U | 3/1977 |
| JP | H06-508551 A | 9/1994 |
| JP | 2015-157252 A | 9/2015 |
| JP | 2017-506895 | 3/2017 |
| JP | 2020-526187 A | 8/2020 |
| KR | 20110064080 A | 6/2011 |
| WO | WO-2013/056469 A1 | 4/2013 |
| WO | WO-2015/126589 | 8/2015 |

OTHER PUBLICATIONS

Extended European Search Report dated Aug. 29, 2023 issued in EP Application No. 23167004.3, 8 pages.
Final Office Action on U.S. Appl. No. 15/087,826 Dtd Apr. 13, 2018.
First Examination Report dated Feb. 19, 2023 issued in CN Application No. 201880054283.4, with English translation, 20 pages.
Foreign Action other than Search Report on AU 2016357087 Dtd Nov. 5, 2021.
Foreign Action other than Search Report on AU 2016357087 Dtd Jul. 19, 2021.
Foreign Action other than Search Report on CN 201680078727.9 Dtd Apr. 16, 2021.
Foreign Action other than Search Report on CN 201680078727.9 Dtd Aug. 13, 2020.
Foreign Action other than Search Report on CN 201680078727.9 Dtd Sep. 24, 2021.
Foreign Action other than Search Report on IN 202017002955 Dtd Jun. 22, 2022.
Foreign Action other than Search Report on JP 2018-525673 Dtd Dec. 15, 2020.
Foreign Action other than Search Report on JP 2019-571584 Dtd Apr. 21, 2022.
Foreign Action other than Search Report on SG 11201913149P Dtd Jul. 7, 2021.
International Preliminary Report on Patentability and Transmittal received in corresponding International Application No. PCT PCT/US2018/039269 Dtd Jan. 9, 2020, 7 pages.
International Preliminary Report on Patentability in corresponding International Application No. PCT/US2016/046603, mailed May 22, 2018, 7 pages.
International Search Report and Written Opinion for PCT/US2016/046603 mailed Nov. 15, 2016.
Non-Final Office Action on U.S. Appl. No. 16/017,014 Dtd Dec. 21, 2020.
Non-Final Office Action on U.S. Appl. No. 16/213,520 Dtd Jan. 23, 2019.
Notice of Allowance on U.S. Appl. No. 15/087,826 Dtd Aug. 8, 2018.
Notice of Allowance on U.S. Appl. No. 16/017,014 Dtd Apr. 14, 2021.
Notice of Allowance on U.S. Appl. No. 16/213,520 Dtd May 1, 2019.
Notice of Allowance on U.S. Appl. No. 17/398,829 Dtd Nov. 9, 2023.
Notice of Reasons for Rejection dated Jan. 31, 2023 issued in JP Application No. 2019-571584, with English translation, 3 pages.
Notice to File an Amendment dated Jun. 25, 2018 issued in KR Application No. 10-2018-7017118, with English translation, 4 pages.
Office Action dated Jul. 14, 2023 issued in KR Application No. 10-2020-7002417, with English translation, 5 pages.
Office Action dated Sep. 28, 2022 issued in CA Application No. 3,005,861, 4 pages.
Office Action in correspondence Japanese application No. 2018-525673 dtd Apr. 7, 2020, (3 pages) and English translation (2 pages).
Preliminary Rejection dated Apr. 7, 2023 issued in KR Application No. 10-2018-7017118, with English translation, 13 pages.
Preliminary Rejection dated Jan. 5, 2023 issued in KR Application No. 10-2020-7002417, with English translation, 14 pages.

(56) References Cited

OTHER PUBLICATIONS

Search Report on Singapore Patent Application No. 11201913149P dated Jul. 1, 2021 2 Pages.
Second Office Action dated Oct. 26, 2023 issued in CN Application No. 201880054283.4, with English translation, 14 pages.
US Office Action for U.S. Appl. No. 15/087,826 dated Dec. 11, 2017. (7 pages).
US Office Action for U.S. Appl. No. 15/087,826 dated Jul. 10, 2017. (11 pages).
US Office Action on U.S. Appl. No. 17/398,829 Dtd Jul. 31, 2023.
Rejection Decision dated Mar. 1, 2024 issued in CN Application No. 201880054283.4, with English translation, 16 pages.
International Search Report and Written Opinion dated Sep. 13, 2018, for application No. PCT/US2018/039269, 11 pages.
Notice of Reasons for Refusal for JP Patent App. No. 2023-097690 dated Jul. 23, 2024, with English translation, 12 pages.
Re-Examination Notification dated Jul. 10, 2024 issued in CN Application No. 201680078727.9, with English Machine Translation, 12 pages.
Search Report dated May 24, 2024 issued in SG Application No. 10202106157P, 2 pages.
Written Opinion dated May 28, 2024 issued in SG Application No. 10202106157P, 6 pages.
Foreign Action other than Search Report for CA Appl. Ser. No. 3068618 dated Aug. 22, 2024, 4 pages.

\* cited by examiner

AUTOMATED METHOD AND APPARATUS FOR PREPARING BIOPROCESS SOLUTIONS

CROSS-REFERENCE TO RELATED APPLICATIONS

This application is a divisional of U.S. patent application Ser. No. 17/398,829, filed Aug. 10, 2021, which is a divisional of U.S. patent application Ser. No. 16/017,014, filed Jun. 25, 2018, now U.S. Pat. No. 11,097,237, which claims priority to U.S. Provisional Patent Application Ser. No. 62/527,878, filed Jun. 30, 2017, which applications are each incorporated herein by reference in its entirety.

BACKGROUND

Embodiments of the present technology generally relate to an automated method and apparatus for mixing at least one material with at least one fluid. More particularly, embodiments of the present technology relate to an automated method and apparatus specifically adapted for reconstituting dry ingredients in predetermined unit volume amounts into bioprocess solutions.

A bioprocess is a process that uses living cells or their components to obtain desired products. Bioprocesses often require the use of various solutions. For example, the initial steps in a bioprocess may involve cell culturing, and cell culturing often requires the use of cell culture media to successfully cultivate new cells. Later steps in a bioprocess may then require the use of various buffer solutions as part of a product purification process.

Bioprocess solutions are often hydrated from dry ingredients immediately before use either in large stainless steel tanks or in single-use mixing devices. The typical process is time consuming, expensive and adds no direct value to the desired product.

While the basic cell culture methods have not changed appreciably over the years, the volumes of cell cultures continue to increase dramatically, thereby changing the requirements for media preparation. Not only are more research laboratories, pharmaceutical, and biotechnology companies employing cell culture methods, but they are often doing so on a very large scale. A biotechnology company may consume many thousands of liters of liquid media a day and employ large numbers of manufacturing technicians and scientists to produce antibodies, growth factors, or recombinant proteins from cell culture for commercial use. The present invention provides an automated system and method for employing an in-line mixing device to prepare bioprocess solutions that can help reduce the required time, labor, risk of error and risk of contamination in these processes while also improving reliability and consistency.

SUMMARY OF THE INVENTION

Generally, embodiments described herein relate to automated methods and apparatuses for preparing dry ingredients into liquid solutions (e.g., preparing powdered bioprocess media into liquid bioprocess media). As discussed further below, dry ingredients tend to require less storage space than reconstituted, liquid solutions, have longer shelf lives, be less expensive, and require less shipping and handling time than prepackaged liquid solutions. Thus, when liquid solutions are needed, it is advantageous to utilize automated methods and apparatuses designed to make the preparation of liquid solutions from dry ingredients simple, straightforward, and repeatable, rather than purchase prepackaged liquid solutions. Accordingly, the technology according to some embodiments relates to an automated method to be used with a mixing apparatus for mixing dry ingredients (e.g., a powdered media) into a fluid, such as cell culture media or buffers. More particularly, some embodiments of the present technology relate to an automated method to be used with a mixing apparatus where both the automated method and the mixing apparatus are adapted for reconstituting dry ingredients into liquids in predetermined unit volume amounts.

A variety of dry ingredients may be reconstituted into liquid solutions using the present technology. For example, as used herein, dry ingredients may refer to powdered cell culture media, dry powder media, dry buffer powder, granulated media, dry salts, dry chemicals, dry components, dry materials, and unhydrated ingredients.

Some embodiments described herein are based, at least in part, upon some deficiencies and/or inconveniences with existing reconstitution technologies, as recognized by the inventors of the instant technology, or based upon the recognition of potential improvements by the inventors. For example, prepackaged liquid cell culture media can be sterile and aliquoted into convenient sizes and may come ready to use. However, prepackaged liquid cell culture media are typically light-sensitive and have a prescribed shelf-life. Therefore, prepackaged liquid cell culture media must be ordered on a regular basis. They also should be stored under refrigeration and, in their prepackaged form, require significant manpower time to un-package and transport. Further, shipping costs of prepackaged liquid cell culture media are becoming increasingly more expensive.

By contrast, powdered cell culture media are provided in bulk or in premeasured packages. They tend to have a longer shelf life, be less expensive, and require less storage space and shipping and handling time than when in liquid form. However, powdered cell culture media must be reconstituted into liquid cell culture media by aliquoting and dissolving the powdered media under sterile conditions. The increased handling and preparation time for powdered cell culture media, especially for large volume media preparation, often makes prepackaged liquid cell culture media the preferred choice despite the increased cost.

Furthermore, reconstitution of dry ingredients into a liquid bioprocess solution generally is a several step process. As an example, to prepare liquid cell culture media from a solid powder, a known amount of powder intended for a specific volume of media is measured out and added to a volume of distilled water that is typically less than the final desired volume. The powder and water are stirred until the solid is completely dissolved. A specific quantity of sodium bicarbonate is added and dissolved. The pH may thereafter be adjusted using an acid or base, and additional water is added to increase the media to its final volume. The entire mixture is then passed through a sterilizing filter. The media may thereafter be collected in a single large sterile vessel or proportioned into several smaller sterile vessels.

There may be further difficulties in reconstituting solutions based on characteristics of the dry ingredients being reconstituted. For example, powdered tissue culture media have very fine particle sizes and are hygroscopic. When mixed with water, they have the tendency to "ball" or "clump." Thus, when reconstituting in water or another aqueous liquid, sufficient agitation is required to break up any clumps that may form upon initial contact with water. For smaller batch sizes, sterile magnetic stir bars can be added to the mixing container, and the container is then placed on a magnetic stir plate. Additional manipulations usually are required to add stir bars to the mixing containers. In a typical laboratory setting, however, magnetic stir plates are not a practical solution for large volume media preparation.

In addition, due to their hygroscopic nature, powdered cell culture media absorb water when stored, especially in humid environments. Wet powdered media have shortened shelf lives, become lumpy, and require aggressive agitation to reconstitute. Thus, powdered cell culture media shelf life could be improved if they were provided in premeasured, sealed, and desiccated aliquots.

Further, the reconstitution process requires several steps and several separate pieces of equipment. It generally requires at least one vessel, large enough to contain the entire final volume of reconstituted media, plus one or more vessels to receive the sterile media after filtration. The sterilized media are usually delivered into open top containers. Thus, most media preparation is done in a laminar flow hood. Processing large volumes of media in a hood is difficult, however, because there is often not enough space to accommodate the containers and sterile media. Accordingly, a method and a device permitting the preparation of large volumes of solutions (e.g., cell culture media) with minimal physical contact and in a reliable and repeatable way are described herein.

One embodiment of the technology relates to an automated method. The automated method includes providing a dry ingredient to be reconstituted into a liquid bioprocess solution and controlling, by a processing circuit, an automated system including at least one mixing chamber, an array of tubing for fluid flow within the system, and a plurality of valves provided within the tubing, to automatically prepare the liquid bioprocess solution from the dry ingredient. Controlling the automated system may include performing a series of sequential mixing steps, the series of sequential mixing steps causing the preparation of the liquid bioprocess solution. The method may further include taking one or more measurements during the preparation of the liquid bioprocess solution, wherein each step is triggered by at least one of a measurement decreasing below, equaling, or exceeding a measurement threshold. Each step may also include opening or closing, by the processing circuit, at least one of the plurality of valves to control fluid flow within the automated system. The bioprocess solution may be cell culture media or a buffer solution.

A second embodiment of the technology relates to an automated method. The automated method includes providing a dry ingredient to be reconstituted into a liquid bioprocess solution and providing an automated system including at least one mixing chamber, an array of tubing for fluid flow within the system, a plurality of valves provided within the tubing, and one or more inlets to the tubing. The automated method also includes coupling a purified water sources to one of the one or more inlets. The automated method further includes controlling, by a processing circuit, the automated system to prepare a liquid bioprocess solution from the dry ingredient by performing a series of sequential mixing steps, each step comprising opening or closing at least one of the plurality of valves to control fluid flow within the automated system, and taking one or more measurements during the preparation of the liquid bioprocess solution, wherein each step is triggered by at least one of a measurement decreasing below, equaling, or exceeding a measurement threshold. The bioprocess solution may be cell culture media or a buffer solution.

A third embodiment of the technology relates to an automated apparatus for preparing a liquid bioprocess solution from a dry ingredient. The automated apparatus includes at least one mixing chamber, an array of tubing, a plurality of valves provided within the tubing, and a mixing controller. The mixing controller includes at least a processor and a memory with instructions stored thereon, the mixing controller configured to control the plurality of valves to prepare a liquid bioprocess solution from a dry ingredient. The automated apparatus may also include one or more sensors configured to take one or more measurements during preparation of the liquid bioprocess solution, wherein the mixing controller is configured to control the plurality of valves in response to at least one of a measurement decreasing below, equaling, or exceeding a measurement threshold. The bioprocess solution may be cell culture media or a buffer solution.

A fourth embodiment of the technology relates to an automated method. The automated method includes providing a bioprocessing buffer in a dry format and controlling, by a processing circuit, an automated system comprising at least one mixing chamber, an array of tubing for fluid flow within the system, and a plurality of valves provided within the tubing, to automatically prepare a liquid bioprocessing buffer from the bioprocessing buffer in the dry format. Controlling the automated system may include performing, by the processing circuit, a series of sequential mixing steps, the series of sequential mixing steps causing the preparation of the liquid bioprocessing buffer. The method may further include taking one or more measurements during the preparation of the liquid bioprocessing buffer, wherein each step is triggered by at least one of a measurement decreasing below, equaling, or exceeding a measurement threshold. Each step may also include opening or closing, by the processing circuit, at least one of the plurality of valves to control fluid flow within the automated system.

BRIEF DESCRIPTION OF THE DRAWINGS

The above-mentioned features, as well as other features, aspects, and advantages, of the present technology will now be described in connection with various embodiments of the invention, in reference to the accompanying drawings. The illustrated embodiments, however, are merely examples and are not intended to limit the invention.

DETAILED DESCRIPTION

Figure 1A:
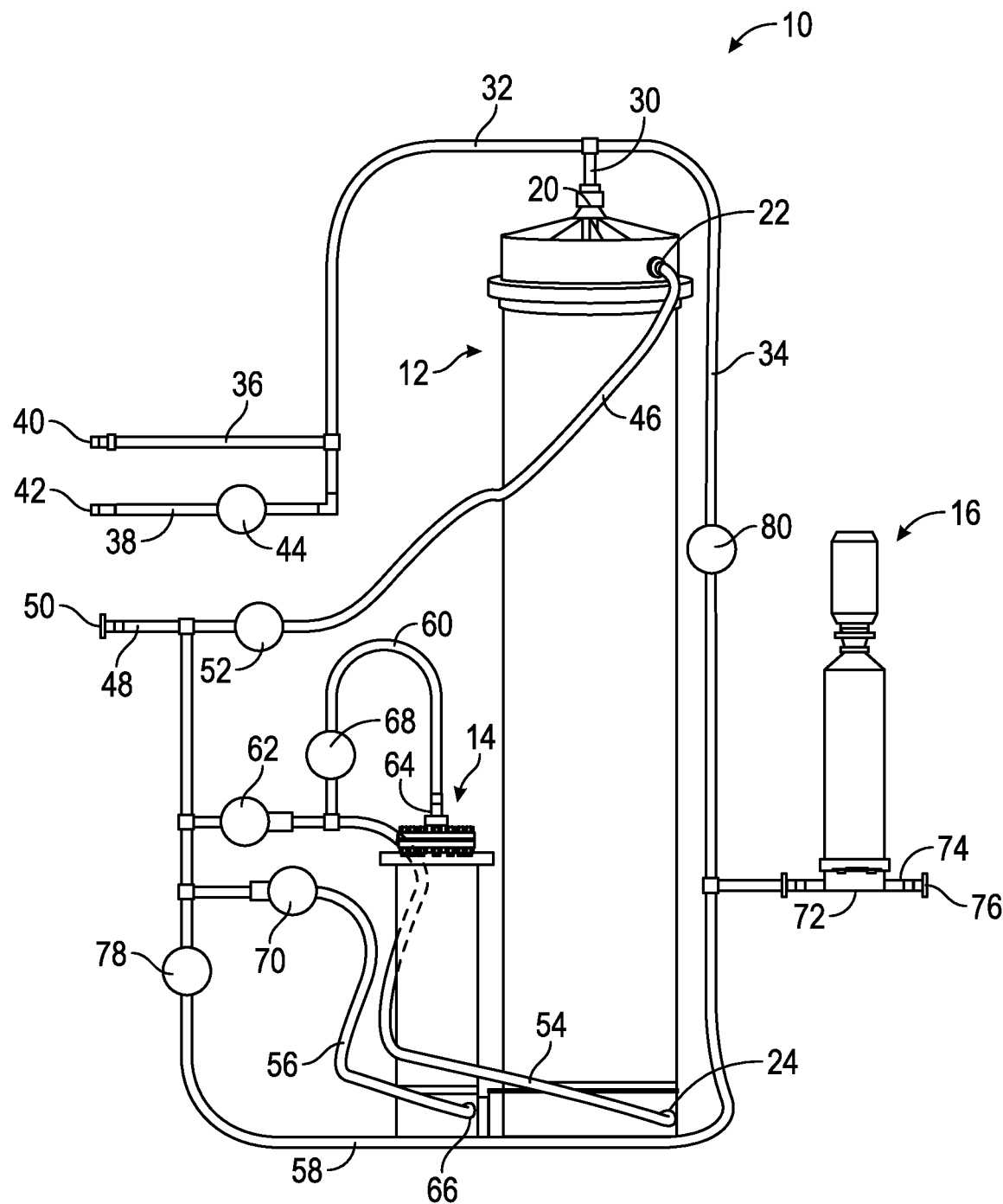
FIGS. 1A and 1B are schematic representations of a mixing apparatus to be used with an automated reconstitution method for a bioprocess solution.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments that may be practiced. The term "exemplary," as used herein, means "serving as an example, instance, or illustration" and should not necessarily be construed as preferred or advantageous over other embodiments. Other embodiments may be utilized, and other changes may be made, without departing from the spirit or scope of the subject matter presented herein. It will be readily understood that the aspects of the present disclosure, as generally described herein and illustrated in the Figures, can be arranged, substituted, combined, and designed in a wide variety of different configurations, all of which are explicitly contemplated and form part of this disclosure.

Embodiments described herein generally relate to devices/apparatuses, systems, and methods for the preparation of solutions from dry ingredients, for example, media for cell culture from dry powdered cell culture media or buffer solutions from dry buffer powder. One or more of the provided embodiments may overcome one or more of the drawbacks, limitations, or deficiencies that exist in the art with respect to reconstituting solutions, particularly with respect to reconstituting cell culture media in a dry format, including dry powder media. For example, in some embodiments described herein, an automated method and apparatus may permit mixing of dry ingredients into a liquid bioprocess solution such that the mixing process is easy to use, can be used to reconstitute relatively large quantities of solution, and results in a solution that is thoroughly mixed and not clumped.

The present disclosure makes reference to the systems and methods described herein in the context of preparing liquid cell culture media from powdered cell culture media. However, it should be understood that the systems and methods described herein can be adapted to preparing other types of solutions. For example, the systems and methods described herein may be used to prepare buffers for chromatography and downstream processing of biopharmaceutical bulk drug substances. As another example, the systems and methods described herein may be used to prepare various "bioprocess solutions," or solutions that are used in processes of using living cells or their components to obtain desired products. Moreover, it is contemplated that the systems and methods described herein may be adapted for a number of broader commercial or industrial applications. As an example, many liquid pharmaceuticals are prepared in the hospital pharmacy with some frequency and quantity. Saline solutions, alimentary preparations, imaging reagents, dyes, sterilization solutions, and anesthetics are reconstituted as liquids. Additional alternative applications include, but are not limited to, preparation of pesticides, fertilizers, and any of a variety of beverages commonly prepared from powder (e.g., milk, iced tea, etc.), all of which could be reconstituted using embodiments of the systems and methods described herein. In this regard, dry ingredients that may be reconstituted using the present systems and methods are not limited to powdered cell culture media and may include dry powder media, dry buffer powder, granulated media, dry salts, dry chemicals, dry components, dry materials, and unhydrated ingredients.

FIG. 1A is an overall system view of one embodiment of a mixing apparatus 10. Preferably, the mixing apparatus 10 is made of materials that are appropriate for the cell culture environment, such as non-toxic, medical grade plastics or other non-toxic materials that will not contaminate the media. The mixing apparatus 10 includes a first mixing chamber 12, a second mixing chamber 14, and a filter unit 16 connected together with various lengths of tubing (e.g., flexible hoses). As discussed in further detail below, the tubing further includes various valves provided therein for selectively allowing (e.g., when the valve is in an open position) and stopping (e.g., when the valve is in a closed position) the flow of fluids through the valves. In an exemplary embodiment, the valves are pinch valves, though in other embodiments, the valves may be or include other types of valves, such as ball valves. In various embodiments, the mixing apparatus 10 is designed for reconstitution of powdered cell culture media into liquid media. For example, the mixing apparatus 10 may be a single use apparatus with necessary media components (e.g., powdered cell culture media, sodium bicarbonate, etc.) prepackaged therein. However, those of skill in the art will appreciate that the mixing apparatus 10 may also be used to reconstitute other forms of undissolved cell culture media (e.g., granulated cell culture media), prepare bioprocessing buffers from a dry format, or more generally reconstitute liquids from powders.

To begin with, in various embodiments, the first mixing chamber 12 contains dry powder media to be reconstituted into liquid media. It is contemplated that the first mixing chamber 12 will be provided with a premeasured amount of dry powder media. In some embodiments, the first mixing chamber 12 may be prepackaged with the premeasured amount of dry powder media already therein. Additionally, in various embodiments, the first mixing chamber 12 is designed to facilitate mixing of the media with purified water and/or with other powders or liquids, such as dissolved sodium bicarbonate or a supplement. For example, the first mixing chamber 12 may include a top and/or bottom cone coupled to the top and/or bottom end, respectively, of the first mixing chamber 12 to facilitate the creation of a swirling vortex motion as fluid enters the first mixing chamber 12. The swirling vortex motion helps facilitate the mixing of the dry powder media, the purified water, dissolved sodium bicarbonate, a supplement, etc. Various configurations and embodiments of the first mixing chamber 12 are described in U.S. application Ser. No. 15/087,826 titled "Media Mixing Chamber," filed on Mar. 31, 2016, and hereby incorporated herein in its entirety.

The first mixing chamber 12 includes three ports whereby fluids may flow into and out of the first mixing chamber 12: a top port 20, an upper port 22, and a lower port 24. In exemplary embodiments, the ports 22 and 24 are positioned on the first mixing chamber 12 such that fluids enter the first mixing chamber 12 through the ports 22 and 24 at substantially a tangential angle to an inner wall of the first mixing chamber 12, which may further facilitate the mixing of various media components in the first mixing chamber 12.

A top inlet/outlet tube 30 is coupled to the first mixing chamber 12 at the top port 20. As shown in FIG. 1A, the top inlet/outlet tube 30 connects the first mixing chamber 12 to a common inlet tube 32 and an upper filter inlet tube 34. In turn, the common inlet tube 32 connects to a supplement inlet tube 36 and a compressed air inlet tube 38. The supplement inlet tube 36 is configured to couple to a supplement source (not shown) at a supplement entry 40. The supplement source may contain any type of supplement used in cell culture media, such as an amino acid supplement, a cholesterol supplement, a lipid supplement, etc. The compressed air inlet tube 38 is configured to couple to a compressed air source (not shown) at a compressed air entry 42. Accordingly, when fluids (e.g., media supplements, compressed air) are introduced to the apparatus 10 by the supplement inlet tube 36 and by the compressed air inlet tube 38, the fluids flow to the common inlet tube 32. The fluids then flow to the top inlet/outlet tube 30 and into the first mixing chamber 12 by the top port 20.

As shown in FIG. 1A, the compressed air inlet tube 38 also includes a compressed air valve 44. When in an open position, the compressed air valve 44 allows compressed air to flow from the compressed air source through the compressed air valve 44 to the first mixing chamber 12, as described. Conversely, when the compressed air valve 44 is in a closed position, the compressed air valve 44 prevents compressed air from flowing through the valve 44. However, as further shown in FIG. 1A, the supplement inlet tube 36 does not include a valve. Thus, unlike compressed air, supplement is able to flow to the first mixing chamber 12 whenever supplement is introduced to the apparatus 10 by the supplement inlet tube 36.

An upper inlet tube 46 is coupled to the first mixing chamber 12 at the upper port 22. The upper inlet tube 46 connects to a fluid inlet tube 48. The water inlet tube 48 is configured to couple to a fluid source (not shown) by a fluid entry 50. In an exemplary embodiment, the fluid source contains and provides purified water (e.g., distilled deionized water ($ddH_2O$)). In an exemplary embodiment, the water source contains at least 1,000 L of purified water. Additionally, the upper inlet tube 46 includes an upper inlet valve 52. As such, when the upper inlet valve 52 is in an open position and water is introduced to the apparatus 10 by the water inlet tube 48, the water flows from the water inlet tube 48, through the open upper inlet valve 52, and into the upper inlet tube 46. From the upper inlet tube 46, the water flows into the first mixing chamber 12 by the upper port 22. When the upper inlet valve 52 is in a closed position, water cannot flow to the first mixing chamber 12 by the upper port 22.

As shown in FIG. 1A, the water inlet tube 48 further connects to a lower flow tube 54, a second chamber tube 56, and a lower filter tube 58. The lower flow tube 54 is coupled to the first mixing chamber 12 by the lower port 24, and a second chamber outlet tube 60 branches from the lower flow tube 54 partway down the length of the lower flow tube 54. The lower flow tube 54 further includes a lower port valve 62 proximate to the tubing section where the water inlet tube 48, the lower flow tube 54, the second chamber tube 56, and the lower filter tube 58 connect. Thus, when the lower port valve 62 is in an open position, fluids can flow into and out of the first mixing chamber 12 through the lower flow tube 54 and the lower port 24, but when the lower port valve 62 is in a closed position, fluids cannot flow past the valve 62.

The second mixing chamber 14 contains an additive to the cell culture media. In an exemplary embodiment, the second mixing chamber 14 contains sodium bicarbonate powder, and the second mixing chamber 14 is designed to facilitate mixing of the sodium bicarbonate with purified water. Additionally, the second mixing chamber 14 may be prepackaged with a premeasured amount of sodium bicarbonate therein. In some embodiments, the second mixing chamber 14 is configured similarly to the first mixing chamber 12 (e.g., including a top and/or bottom cone coupled to the top and/or bottom end, respectively, of the second mixing chamber 14 to facilitate the creation of a swirling vortex motion as fluid enters the second mixing chamber 14). In other embodiments, the second mixing chamber 14 is configured differently from the first mixing chamber 12. Various configurations and embodiments of the second mixing chamber 14 are described in U.S. application Ser. No. 15/087,826 titled "Media Mixing Chamber," filed on Mar. 31, 2016, which as noted above is incorporated herein in its entirety.

The second mixing chamber 14 includes two ports whereby fluids may flow into and out of the second mixing chamber 14: a second chamber top port 64 and a second chamber lower port 66. In exemplary embodiments, the port 66 is positioned such that fluids enter the second mixing chamber 14 by the port 66 at substantially a tangential angle to an inner wall of the second mixing chamber 14, which may further facilitate the mixing of the sodium bicarbonate and the purified water in the second mixing chamber 14.

As shown in FIG. 1A, the second chamber outlet tube 60 is coupled to the second mixing chamber 14 at the second chamber top port 64. The second chamber outlet tube 60 also includes a second chamber outlet valve 68 proximate to where the second chamber outlet tube 60 branches from the lower flow tube 54. Additionally, as shown in FIG. 1A, the second chamber tube 56 is coupled to the second mixing chamber 14 at the second chamber lower port 66. The second chamber inlet tube 56 further includes a second chamber inlet valve 70 proximate to the tubing section where the water inlet tube 48, the lower flow tube 54, the second chamber tube 56, and the lower filter tube 58 connect. Accordingly, fluids (e.g., purified water from the water source) can only flow into and out of the second mixing chamber 14 when the second chamber inlet valve 70 and the second chamber outlet valve 68 are in open positions. When the second chamber inlet valve 70 and the second chamber outlet valve 68 are in closed positions, fluids cannot flow into or out of the second mixing chamber 14.

The lower filter tube 58 connects the tubing section where the water inlet tube 48, the lower flow tube 54, the second chamber tube 56, and the lower filter tube 58 meet to the upper filter inlet tube 34, at which point the lower filter tube 58 and the upper filter inlet tube 34 merge. The merged lower filter tube 58 and upper filter inlet tube 34 then connect to the filter unit 16. As shown in FIG. 1A, the filter unit 16 includes a filtration tubing section 72 whereby the filter unit 16 couples to the merged lower filter tube 58 and upper filter inlet tube 34. The filtration tubing section 72 is also coupled to an outlet 74, which ends in an apparatus exit 76. The apparatus exit 76 is configured to couple to a collection vessel that collects the media solution mixed and outputted by the apparatus 10. In various embodiments, the collection vessel may be made of glass, plastic, or metal and may be pre-formed or flexible.

The filter 16 is configured to filter solution flowing into the filter by the filtration tubing section 72. For example, the filter 16 may remove undissolved powdered media from the solution by a membrane in the filter 16. The filter 16 may be further configured to sterilize the solution flowing into the filter before the solution flows out of the apparatus by the outlet 74. Additionally, because air will not pass through the membrane of the filter 16 once the filter 16 is wet, the filter 16 may further include a top segment with a hydrophobic vent that allows air to escape the filter 16. This vent prevents air from becoming trapped in the filter 16, hindering the filtration process.

Filters of the type contemplated by this technology can be purchased from a number of suppliers. For example, the filter 16 may comprise nylon or cellulose acetate. Additionally, for a media product, the filter 16 will typically be a 0.2μ filter, though it is contemplated that other filter sizes could be chosen for certain functions. For example, the preparation of electrophoretic buffers requires clean, but not necessarily sterile solutions, and a 0.45μ filter would be adequate. Similarly, the preparation of more viscous solutions may necessitate a wider pore size. In short, the filter 16 can be of any desired size, volume, pore size, and so forth. Moreover, for other applications of the technology disclosed herein, no filtration apparatus may need to be added. Liquid then passes directly to the collection vessel through the outlet 74. Alternatively, in some embodiments, a hydrophobic vent filter is employed at some point before the filter 16 in order to allow the air that is entrained in the dissolved medium to vent so that it does not fill the filter 16.

As shown in FIG. 1A, the lower filter tube 58 further includes a water bypass valve 78 proximate to the tubing section where the water inlet tube 48, the lower flow tube 54, the second chamber tube 56, and the lower filter tube 58 connect. As such, when the water bypass valve 78 is in an open position and the water source is open, fluid flows from the fluid source through the water inlet 48 and into the lower filter tube 58. From the lower filter tube 58, the fluid flows into the filter 16 by the filtration tubing section 72. In this way, fluid may bypass both the first mixing chamber 12 and the second mixing chamber 14 and flow directly to the filter 16 (e.g., to alleviate filter 16 backpressure). When the water bypass valve 78 is in a closed position, the water bypass valve 78 prevents fluids (e.g., water from the water source, bicarbonate solution mixed by the second mixing chamber 14) from bypassing the first mixing chamber 12 and flowing directly to the filter 16.

As also shown in FIG. 1A, the upper filter inlet tube 34 additionally includes an upper filter inlet valve 80. Accordingly, when the upper filter inlet valve 80 is in an open position, the upper filter inlet tube 34 allows the flow of fluids through the upper filter inlet tube 34 to the filter 16. More specifically, when the first mixing chamber 12 fills with solution (e.g., a solution of purified water, powdered media, bicarbonate, and/or a supplement), the solution flows out of the first mixing chamber 12 by the top port 20 and into the top inlet/outlet 30. The solution then flows into the upper filter inlet tube 34 and, when the upper filter inlet valve 80 is in the open position, flows into the filter 16 by the filtration tubing section 72. On the other hand, when the upper filter inlet valve 80 is in a closed position, fluids cannot flow through the upper filter inlet tube 34 to the filter 16.

Figure 1B:
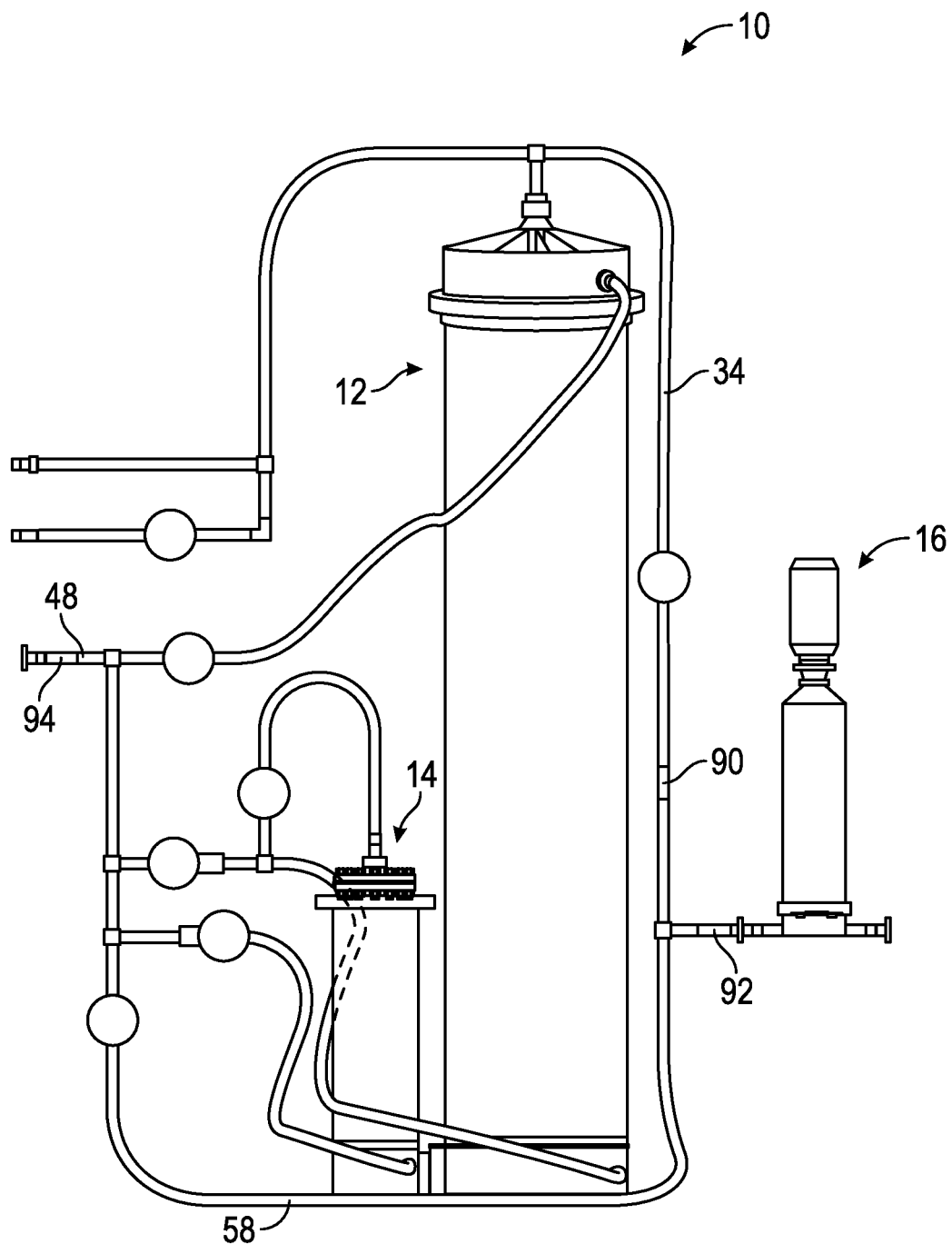

Additionally, in various embodiments, the mixing apparatus 10 may include various sensors for taking measurements in the mixing apparatus 10. These sensors may include, for example, pressure sensors (e.g., for detecting water pressure within the apparatus 10), conductivity sensors (e.g., for detecting the conductivity, and thus the concentration, of solutions in the apparatus 10), volume sensors, such as a rotary flow meter, (e.g., for detecting a volume and flow rate of fluid consumed in the mixing process), pH sensors (e.g., for detecting the pH of solutions in the apparatus 10), viscometers (e.g., for measuring the viscosity of fluids in the apparatus 10), and so on. As shown in FIG. 1B, in an exemplary embodiment, the mixing apparatus 10 includes at least a pressure sensor 90 located in the upper filter inlet tube 34, a conductivity sensor 92 located in the merged upper filter inlet tube 34 and lower filter tube 58, and a volume sensor 94 located in the water inlet tube 48. The pressure sensor 90 is configured to measure the pressure of the fluids flowing into the filter 16 (e.g., to ensure that the filter 16 backpressure does not become too high). The conductivity sensor 92 is configured to measure the conductivity of the solution flowing into the filter 16, thereby indirectly measuring the concentration of the solution flowing into the filter 16 and ultimately out of the apparatus 10. Finally, the volume sensor 94 is configured to measure the volume and flow rate of water consumed during the mixing process.

In various embodiments, as described in further detail below, the powdered media are mixed into liquid media in the mixing apparatus 10 through an automated method. Using the mixing apparatus 10 to prepare liquid media from dry powdered media through an automated method is an improvement over the current field, as it allows for easy and efficient liquid media preparation. Additionally, having programming logic (e.g., implemented by a processing circuit executing instructions stored on non-transitory machine readable media as part of a computing system) controlling the automated method makes the preparation of liquid media from dry powdered media repeatable and consistent.

In an automated method, a computing system controls the opening and closing of valves (e.g., valves 44, 52, 62, 68, 70, 78, and 80), as well as sources of components used during the automated method (e.g., a water source, a compressed air source, a supplement source), to control the mixing of the powdered media into liquid media. The computing system may open and/or close valves and component sources in response to a variety of triggers. For example, the computing system may receive measurements from the mixing apparatus 10 relating to the mixing process (e.g., from the pressure sensor 90, the conductivity sensor 92, and the volume sensor 94). The computing system may then open and/or close valves and/or component sources in response to receiving measurements of certain levels, below or above certain levels, within certain ranges, etc. As another example, the computing system may open and/or close valves and/or component sources in response to certain amounts of elapsed time.

Figure 2:
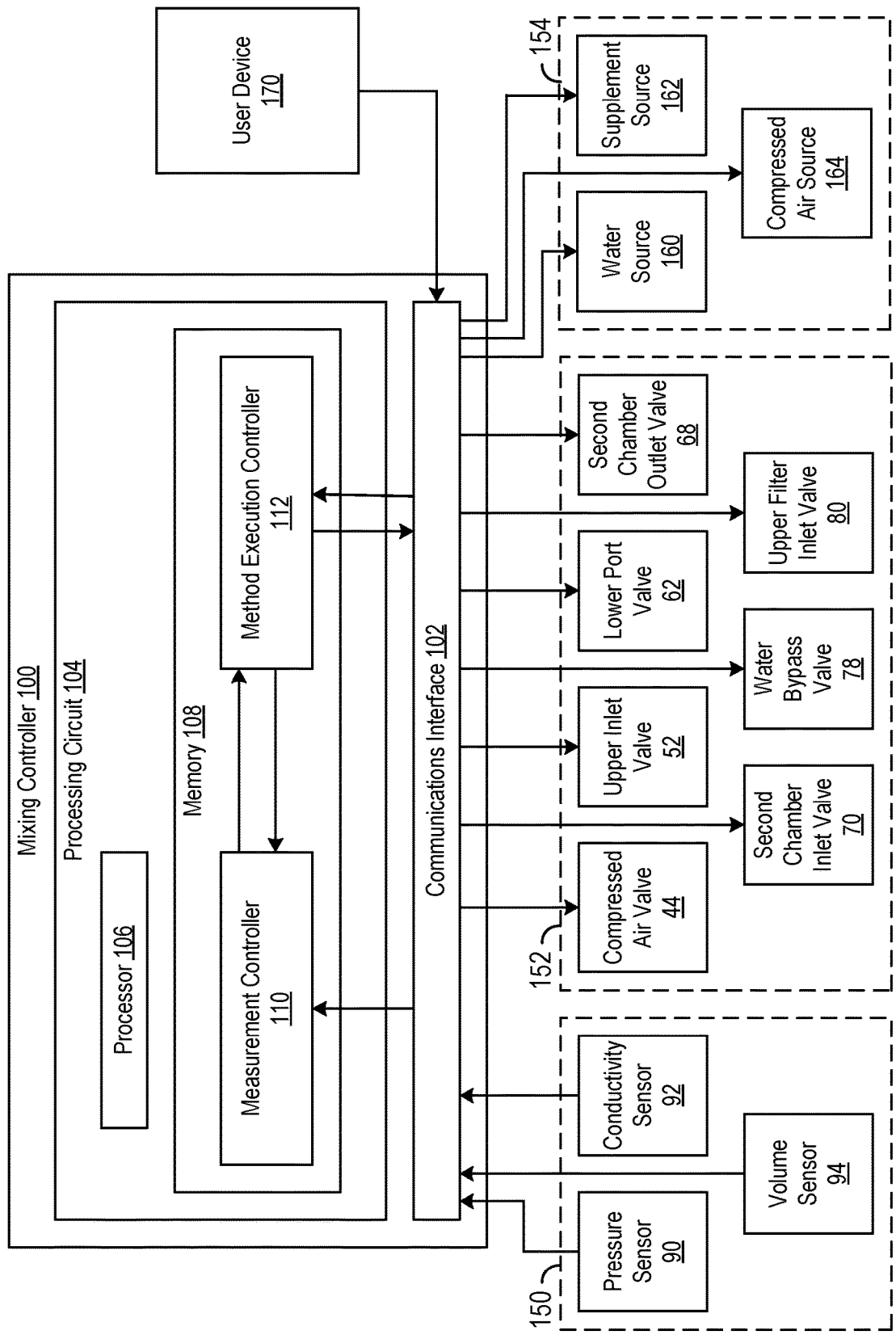
FIG. 2 is a schematic diagram of a mixing controller to be used with the mixing apparatus of FIGS. 1A and 1B.

Accordingly, FIG. 2 illustrates a computing system configured to control the mixing apparatus 10 according to an automated method, the computing system embodied as mixing controller 100. As shown in FIG. 2, the mixing controller 100 includes a communications interface 102 and a processing circuit 104. The communications interface 102 is structured to facilitate communications between the mixing controller 100 and external systems or devices. Thus, as shown in FIG. 2, the communications interface 102 may receive data relating to the mixing process from a group of sensors 150 included in the mixing apparatus 10, such as pressure data from the pressure sensor 90, conductivity data from the conductivity sensor 92, and volume/flow rate data from the volume sensor 94. Additionally, the communications interface 102 may receive commands from a user via a user device 170. For example, the communications interface 102 may receive a command from the user via the user device 170 to begin executing an automatic mixing method.

As further shown in FIG. 2, the communications interface 102 may transmit commands to one or more of a group of valves 152, such as valves 44, 52, 62, 68, 70, 78, and 80 discussed above. Similarly, the communications interface 102 may transmit instructions or commands to a group of component sources 154, such as a water source 160 (e.g., coupled to the water entry 50), a supplement source 162 (e.g., coupled to the supplement entry 40), and a compressed air source 164 (e.g., coupled to the compressed air entry 42). For example, the communications interface 102 may transmit instructions to open or close any valve in the group of valves 152 or any component source in the group of component sources 154.

The communications interface 102 may include wired or wireless communications interfaces (e.g., jacks, antennas, transmitters, receivers, transceivers, wire terminals, etc.) for conducting data communications with external systems or devices. In various embodiments, the communications may be direct (e.g., local wired or wireless communications) or via a communications network (e.g., a WAN, the Internet, a cellular network, etc.). For example, the communications interface 102 can include an Ethernet card and port for sending and receiving data via an Ethernet-based communications link or network. In another example, the communications interface 102 can include a WiFi transceiver for communicating via a wireless communications network or cellular or mobile phone communications transceivers.

The processing circuit 104 includes a processor 106 and a memory 108. Processor 106 may be a general purpose or specific purpose processor, an application specific integrated circuit (ASIC), one or more field programmable gate arrays (FPGAs), a group of processing components, or other suitable processing components. Processor 106 is configured to execute computer code or instructions stored in memory 108 or received from other computer readable media (e.g., CDROM, network storage, a remote server, etc.).

Memory 108 may include one or more devices (e.g., memory units, memory devices, storage devices, etc.) for storing data and/or computer code for completing and/or facilitating the various processes described in the present disclosure. Memory 108 may include random access memory (RAM), read-only memory (ROM), hard drive storage, temporary storage, non-volatile memory, flash memory, optical memory, or any other suitable memory for storing software objects and/or computer instructions. Memory 108 may include database components, object code components, script components, or any other type of information structure for supporting the various activities and information structures described in the present disclosure. Memory 108 may be communicably connected to processor 106 via the processing circuit 104 and may include computer code for executing (e.g., by processor 106) one or more processes described herein. When processor 106 executes instructions stored in memory 108 for completing the various activities described herein, processor 106 generally configures the mixing controller 100 (and more particularly processing circuit 104) to complete such activities.

The mixing controller 100 further includes a measurement controller 110 and a method execution controller 112. As shown in FIG. 2, the measurement controller 110 is configured to receive measurements from the group of sensors 150 via the communications interface 102. Additionally, in various embodiments, the measurement controller 110 is configured with an internal timer for keeping track of elapsed time during the execution of the automated method. The measurement controller 110 provides one or more of the received measurements and/or the tracked elapsed time to the method execution controller 112 during the execution of the automated method. Additionally, the measurement controller 110 may receive data from the method execution controller 112 during the execution of the automated method that indicates the progress of the automated method. For example, the measurement controller 110 may receive, from the method execution controller 112, an indication that a given step of the automated method is currently being carried out.

The method execution controller 112 is configured to provide commands to one or more of the group of valves 152 and group of component sources 154. In various embodiments, the method execution controller 112 provides commands in response to (a) instructions from a user received via the communications interface 102 and (b) data received from the measurement controller 110. In one example, the method execution controller 112 may open and/or close certain valves of group 152 and/or certain component sources of group 154 in response to a user instruction to begin executing the automated method. In a second example, the method execution controller 112 may open and/or close certain valves of group 152 and/or certain component sources of group 154 in response to a received measurement being at a certain level. In a third example, the method execution controller 112 may open and/or close certain valves of group 152 and/or certain component sources of group 154 in response to a certain amount of elapsed time. Additionally, the method execution controller 112 may be further configured to provide feedback data to the measurement controller 110. For example, the method execution controller 112 may provide a notification to the measurement controller 110 indicating that a given step of the automated method has been executed.

Figure 3:
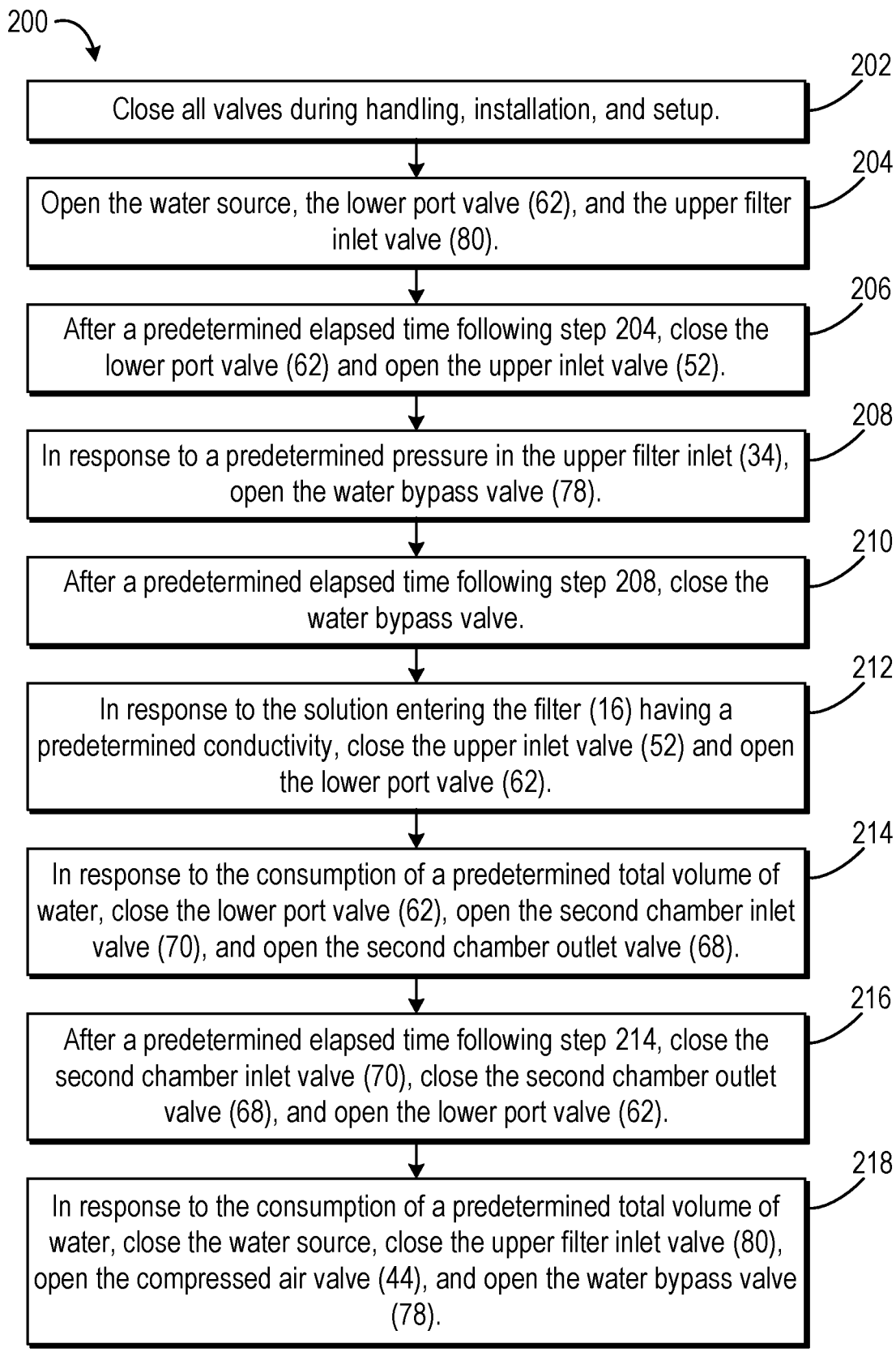
FIG. 3 is a flow diagram illustrating an automated method for reconstituting powdered cell media.

FIG. 3 illustrates a flow diagram depicting an example of an automated method 200 for using the mixing apparatus 10 to mix powdered media into liquid media. FIGS. 4A-4G illustrate the flow of fluids through the mixing apparatus 10 during the steps of the automated method 200. As described below, the sequence of steps illustrated in FIG. 3 and FIGS. 4A-4E set forth a strict protocol for successful use of the mixing apparatus 10 to reconstitute powdered media into liquid media. Use of this strict protocol results in timing that is key to the success of the automated method 200. For example, in an exemplary embodiment, the mixing controller 100 uses the protocol of the automated method 200 to mix a powdered cell culture media volume less than 50% of the volume of the first mixing chamber 12.

However, those of skill in the art will understand that the automated method 200 is meant to be illustrative and does not limit the use of the mixing apparatus 10 to the type and sequence of steps discussed with respect to the automated method 200. Rather, the mixing controller 100 may use other embodiments of automated methods with the mixing apparatus 10 to mix dry media powder into liquid media or, more generally, to mix a dry powder into a liquid. For example, other embodiments of an automated method for use with the mixing apparatus 10 may include the use of different solution components, include fewer or additional steps, include different steps, provide the automated method 200 steps in a different order, and so on. Further, in other embodiments of an automated method for use with the mixing apparatus 10, the steps may include different or additional "triggers" for the steps aside from those discussed below.

To begin with, all of the valves (e.g., valves 44, 52, 62, 68, 70, 78, and 80) are closed during handling, installation, and setup of the mixing apparatus 10 (202). This helps prevent leaking and contamination during the setup process of the mixing apparatus 10. During setup, for example, the first mixing chamber 12 and the second mixing chamber 14, with premeasured amounts of powdered media and sodium bicarbonate provided in chambers 12 and 14, respectively, are unpackaged and set up as shown in FIG. 1A. Alternatively, the first mixing chamber 12 and the second mixing chamber 14 are set up as shown in FIG. 1A and aliquoted amounts of powdered media and sodium bicarbonate are put into the chambers 12 and 14. The first mixing chamber 12 and the second mixing chamber 14 are then configured with the filter 16 and tubing to produce the mixing apparatus 10 as shown in FIG. 1A. Additionally, a compressed air source is coupled to the compressed air entry 42, a purified water source with a fixed quantity of water is coupled to the water entry 50, and, if desired, a supplement source is coupled to the supplement entry 40. A collection vessel is also coupled to the apparatus exit 76.

Figure 4A:
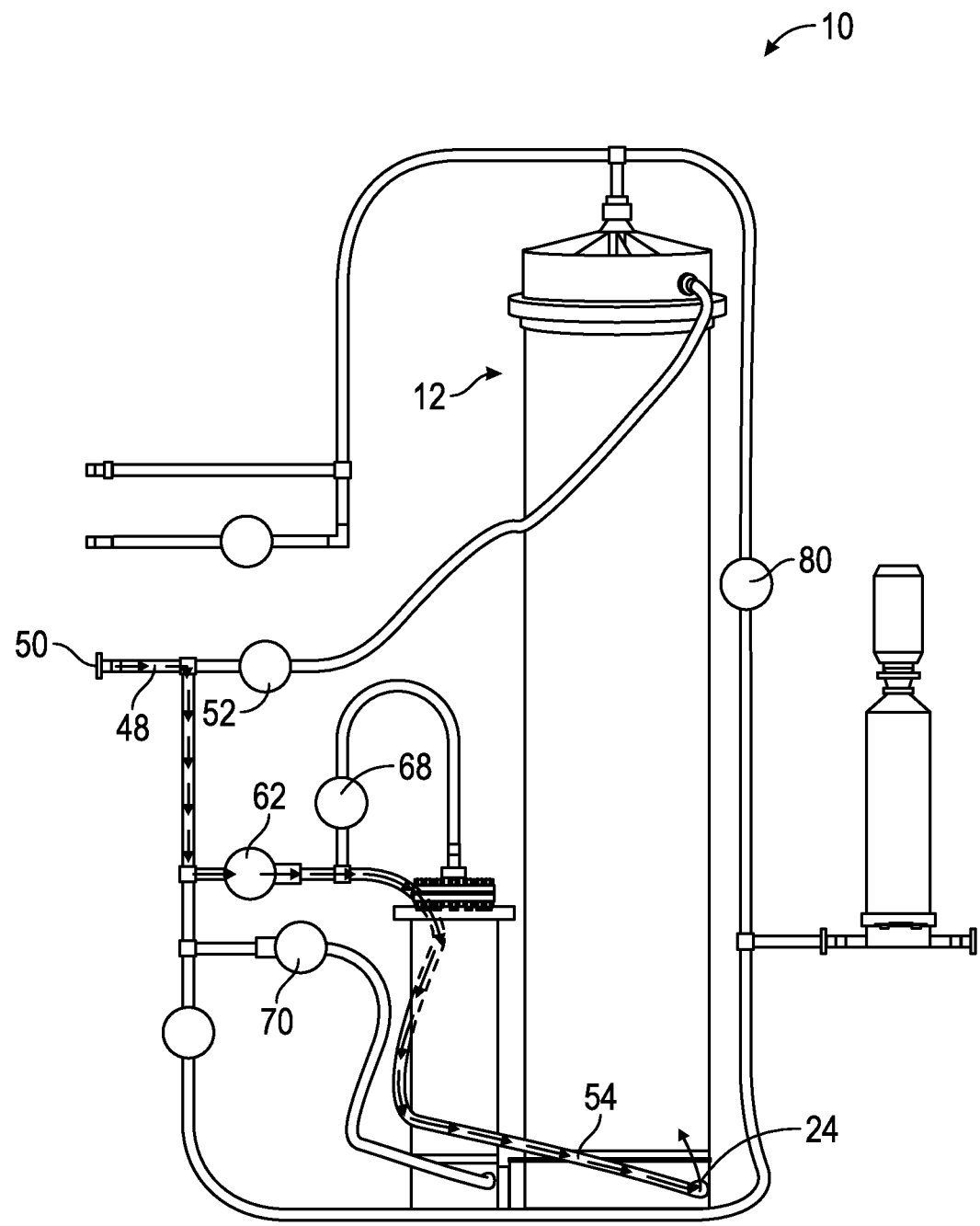
FIGS. 4A-4G are schematic representations of the mixing apparatus of FIGS. 1A and 1B depicting steps of the automated method of FIG. 3.

Next, mixing controller 100 opens the water source, the lower port valve 62, and the upper filter inlet valve 80 (204). As shown in FIG. 4A, once the water source and the lower port valve 62 are opened, water flows from the water source through the water inlet tube 48 and through the lower port valve 62 into the lower flow tube 54. The water then flows from the lower flow tube 54 into the first mixing chamber 12 via the lower port 24, at which point the water begins mixing with the powdered media contained within the first mixing chamber 12.

Figure 4B:
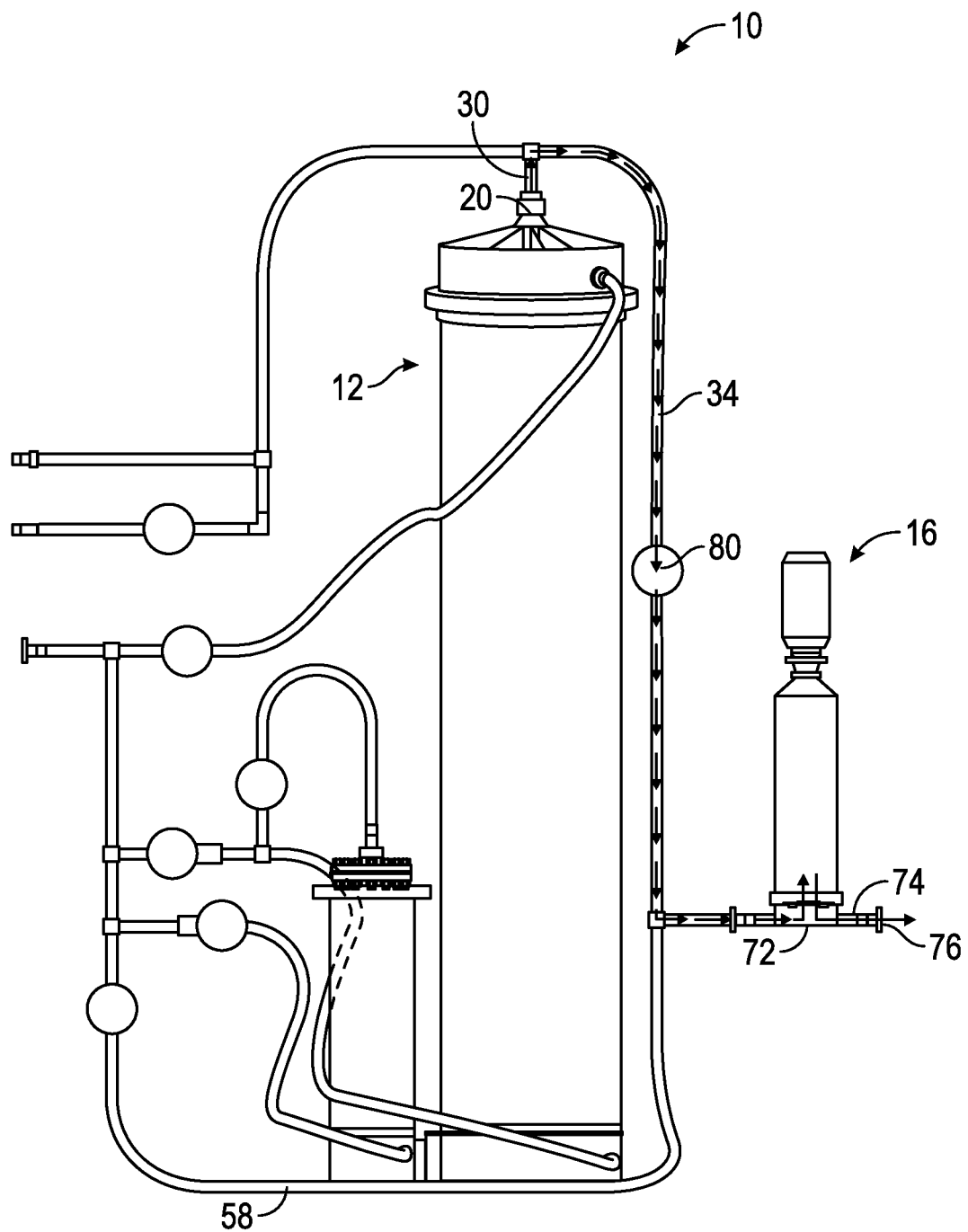

Additionally, because the upper filter inlet valve 80 is open, as the first mixing chamber 12 begins to fill with water from the bottom of the chamber 12, displaced air is evacuated out of the top port 20 of the first mixing chamber 12, as shown in FIG. 4B. The evacuated air flows through the top inlet/outlet 30 and through the upper filter inlet tube 34. The evacuated air leaves the mixing apparatus 10 by flowing through the filter 16 and out of the outlet 74. Alternatively, once the filtering membrane of the filter 16 becomes wet, the membrane may not allow the passage of air through the membrane and through the filter 16. Accordingly, air may instead leave the mixing apparatus 10 by a hydrophobic vent provided in the filter 16 (e.g., provided in a top segment of the filter 16). This is beneficial because it reduces the amount of trapped air in the first mixing chamber 12.

Eventually the water flowing into the first mixing chamber 12 by the lower port 24 and mixing with the powdered media to form media solution fills the first mixing chamber 12. In some embodiments, the first mixing chamber 12 fills with solution soon after the mixing process begins (e.g., during step 204). In other embodiments, the first mixing chamber 12 fills with solution later in the mixing process (e.g., after step 204). Regardless, once this occurs, the solution follows the same path as the evacuated air, as shown in FIG. 4B. The solution leaves the first mixing chamber 12 via the top port 20 and flows through the top inlet/outlet 30, through the upper filter inlet tube 34, and into the filter 16 by the filtration tubing section 72. After being filtered and sterilized by the filter 16, the solution flows into the outlet 74 and flows out of the mixing apparatus 10 through the apparatus exit 76, where it is collected by the collection vessel. Although not shown in FIGS. 4C-4E, once the solution begins flowing out of the first mixing chamber 12 by the top port 20, the solution continues to flow out of the first mixing chamber 12, through the filter 16, and out of the apparatus 10 by the apparatus exit 76 so long as water continues to flow into the first mixing chamber 12 (e.g., until step 216, discussed below).

Figure 4C:
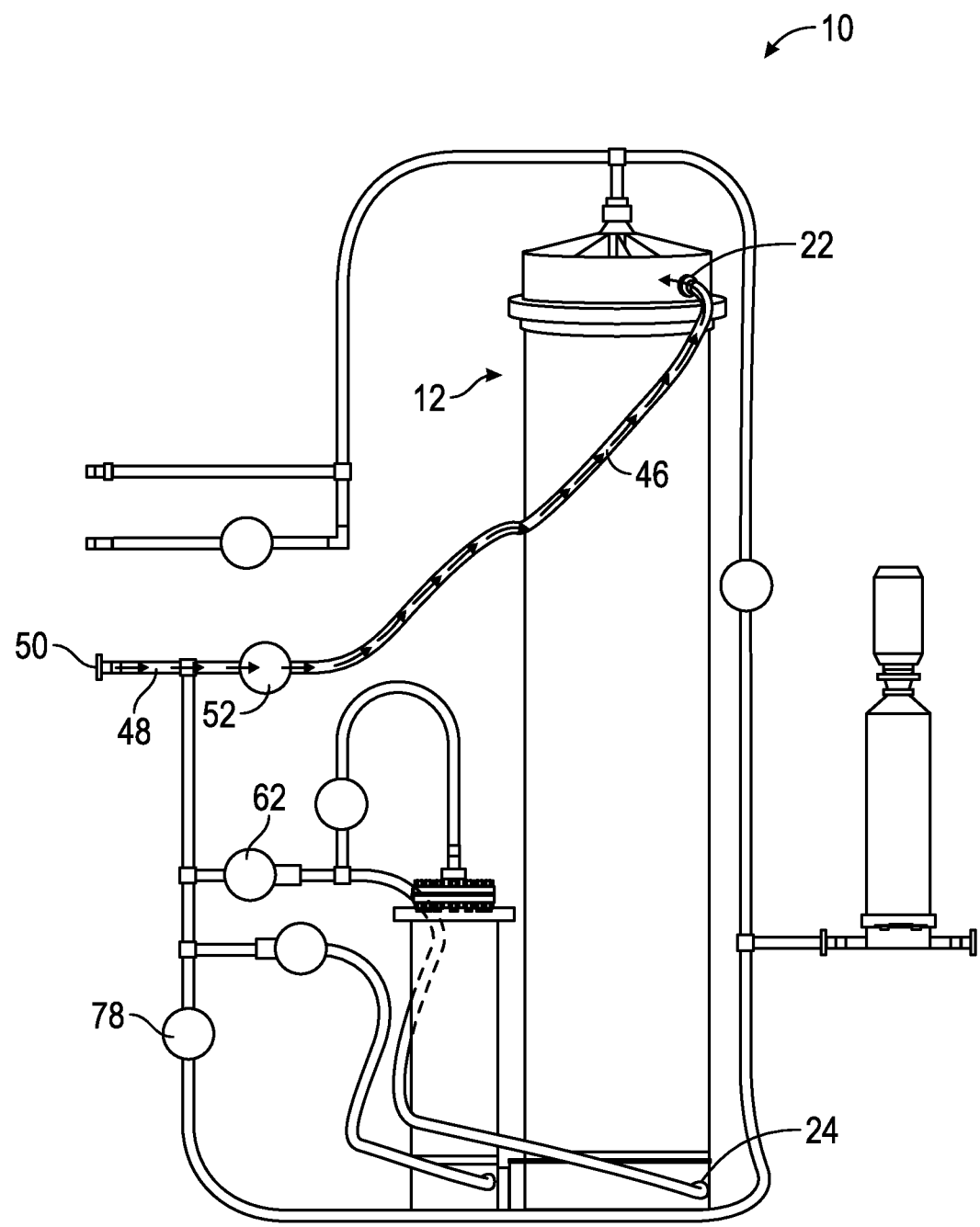

After a predetermined amount of elapsed time, the mixing controller 100 closes the lower port valve 62 and opens the upper inlet valve 52 (206). For example, in one embodiment, the mixing controller 100 waits one minute before closing the lower port valve 62 and opening the upper inlet valve 52. As shown in FIG. 4C, this causes the water to stop flowing into the first mixing chamber 12 by the lower port 24. Instead, the water flows from the water inlet tube 48 to the upper inlet 46. From the upper inlet 46, the water flows into the first mixing chamber 12 by the upper port 22 and continues mixing with the powdered media in the first mixing chamber 12. Switching the flow of water into the first mixing chamber 12 from the lower port 24 to the upper port 22 helps maintain an even dissolution rate of the powdered media in the chamber 12 without overwhelming the filter 16 with high concentrations of solute, undissolved particles, and air, which may happen when the water flows into the chamber 12 by the lower port 24. Additionally, switching the water flow may facilitate a desired and beneficial dissolution rate.

Figure 4D:
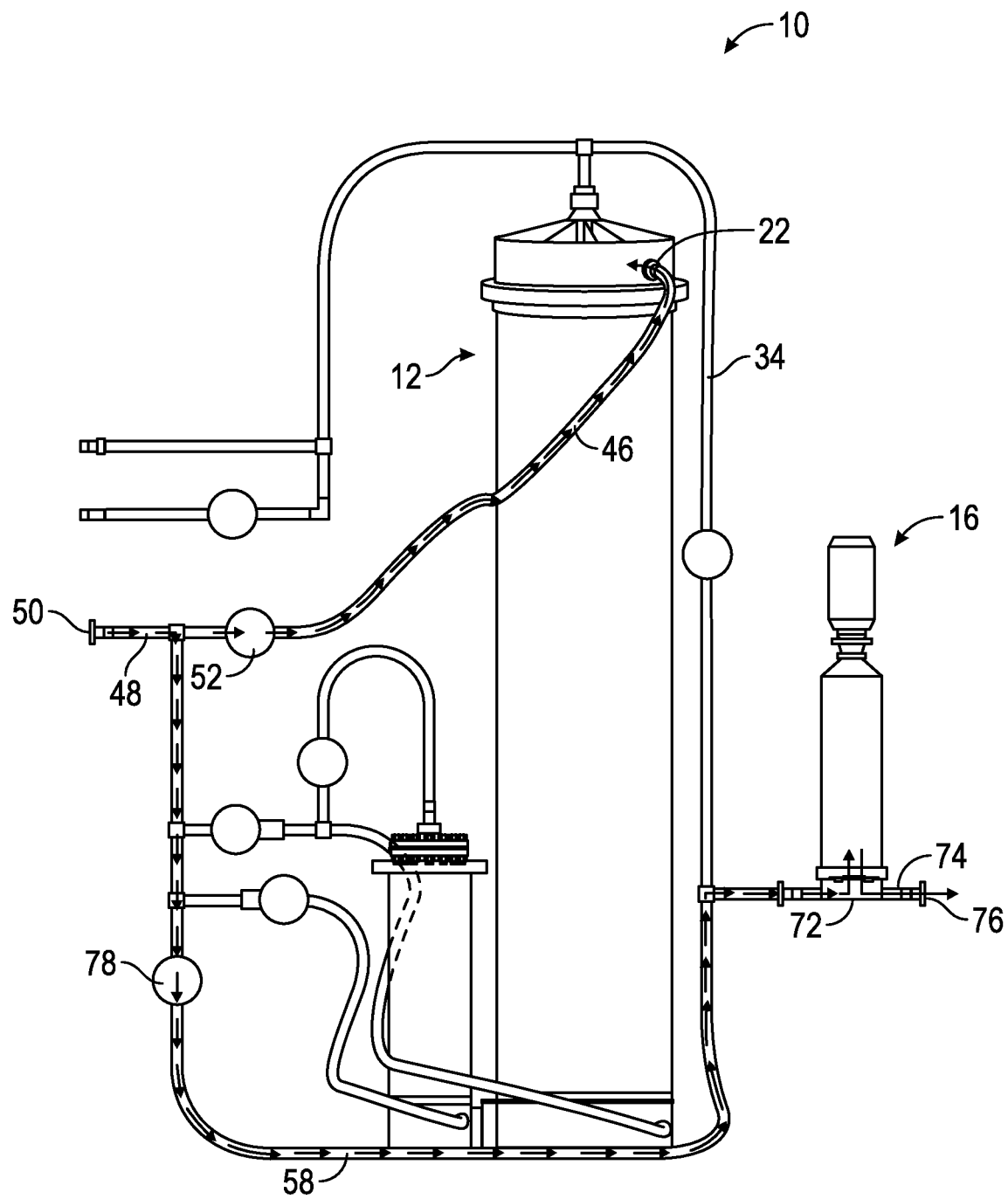

During the above-described steps of the automated method 200, the mixing controller 100 continuously monitors the pressure in the upper filter inlet tube 34 (e.g., by the pressure sensor 90). Once the pressure in the upper filter inlet tube 34 reaches a predetermined level, the mixing controller 100 opens the water bypass valve 78 (208). For example, in one embodiment, the mixing controller 100 opens the water bypass valve 78 when the pressure in the upper filter inlet tube 34 reaches 20 psig. As shown in FIG. 4D, when this occurs, water continues to flow into the first mixing chamber 12 by the upper inlet 46 and the upper port 22. However, water also flows from the water source through the water inlet tube 48 and into the lower filter tube 58. From the lower filter tube 58, the water mixes with solution flowing out of the first mixing chamber 12 (not shown) where the upper filter inlet tube 34 and the lower filter tube 58 merge. Subsequently, the solution flows into the filter 16 by the filtration tubing section 72. After filtration, the water flows out of the apparatus 10 by the outlet 74 and into the collection vessel. Opening the water bypass valve 78, thereby allowing water to bypass the first mixing chamber 12 and the second mixing chamber 14 and flow directly to the filter 16, helps reduce backpressure in the filter 16. It also helps maintain the flow necessary for the first mixing chamber 12 to function properly.

The mixing controller 100 keeps water bypass valve 78 open for a predetermined amount of time, allowing water to flow directly to the filter 16. After the predetermined amount of time has elapsed, the mixing controller 100 closes the water bypass valve 78 (210). For example, in one embodiment, the mixing controller 100 closes the water bypass valve 78 after two minutes have elapsed. Subsequently, the water flow directly to the filter 16 ceases, and the mixing apparatus 10 is switched back to the condition of step 206 as shown in FIG. 4C. By closing the water bypass valve 78, the mixing controller 100 helps avoid premature depletion of the fixed quantity of water required for the automated method 200 (e.g., a fixed quantity of 1,000 L of purified water).

The mixing controller 100 also continuously monitors the conductivity of the solution entering the filter (e.g., by the conductivity sensor 92). Because the solution conductively is related to the solution concentration (e.g., a higher solution conductivity indicates a higher solution concentration and vice versa), monitoring the conductivity of the solution entering the filter allows the mixing controller 100 to indirectly monitor the concentration of the solution exiting the first mixing chamber 12. When the conductivity of the solution reaches a predetermined conductivity, the mixing controller 100 closes the upper inlet valve 52 and opens the lower port valve 62 (212). For example, in one embodiment, the mixing controller 100 closes the upper inlet valve 52 and opens the lower port valve 62 when the conductivity of the solution entering the filter is less than or equal to 6 mS/cm. Accordingly, the water flow into the first mixing chamber 12 switches from the upper port 22 to the lower port 24, returning the mixing apparatus 10 back to the condition of step 204 as shown in FIG. 4A. Switching the flow of the water from the upper port 22 to the lower port 24 when the solution conductivity reaches 6 mS/cm helps ensure that a sufficient concentration of solutes (e.g., powdered media) in the solution mixing in the first mixing chamber 12 is maintained (e.g., such that the fixed quantity of water provided in the water source is not depleted without the depleted water being mixed into a sufficiently concentrated solution).

Figure 4E:
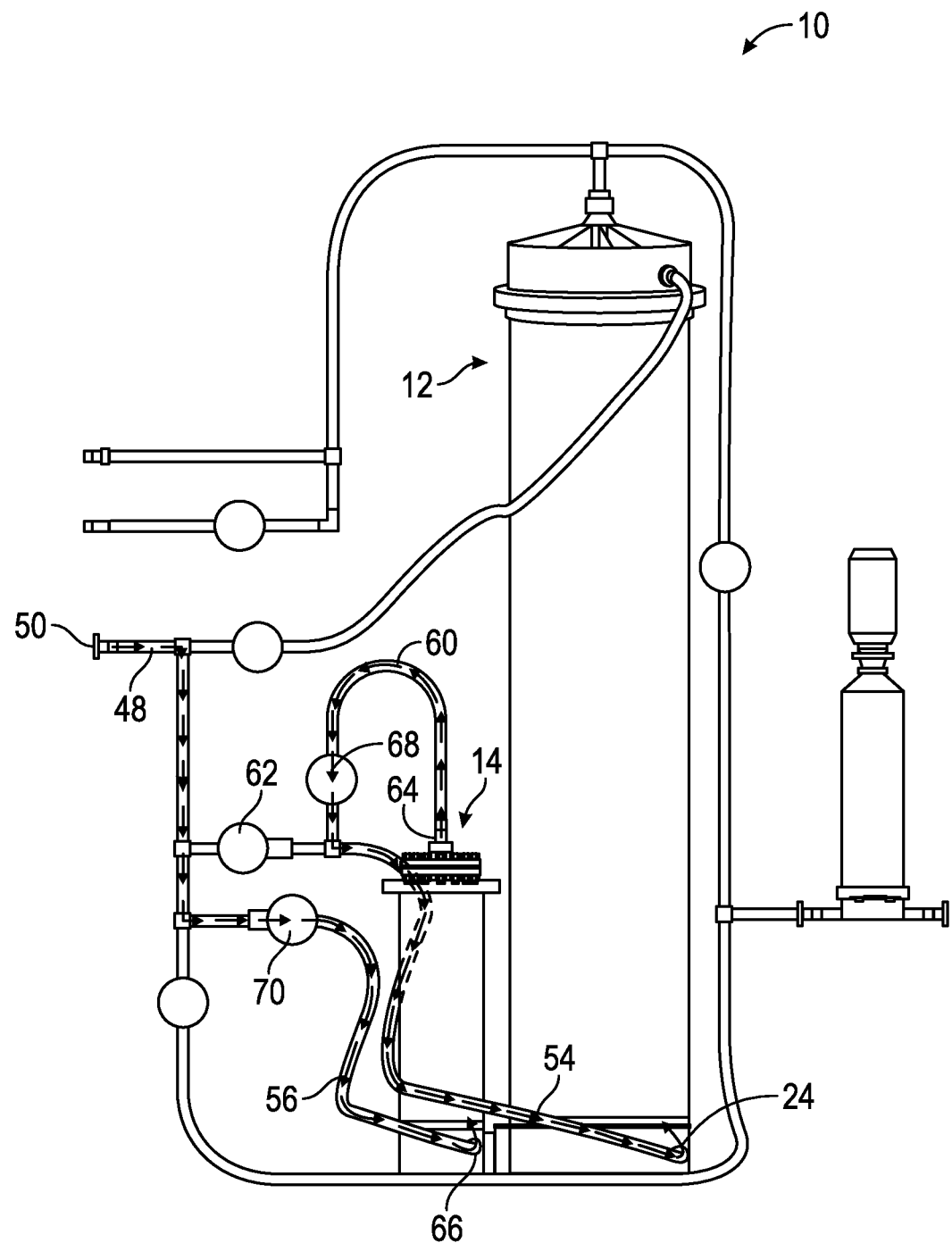
Figure 4F:
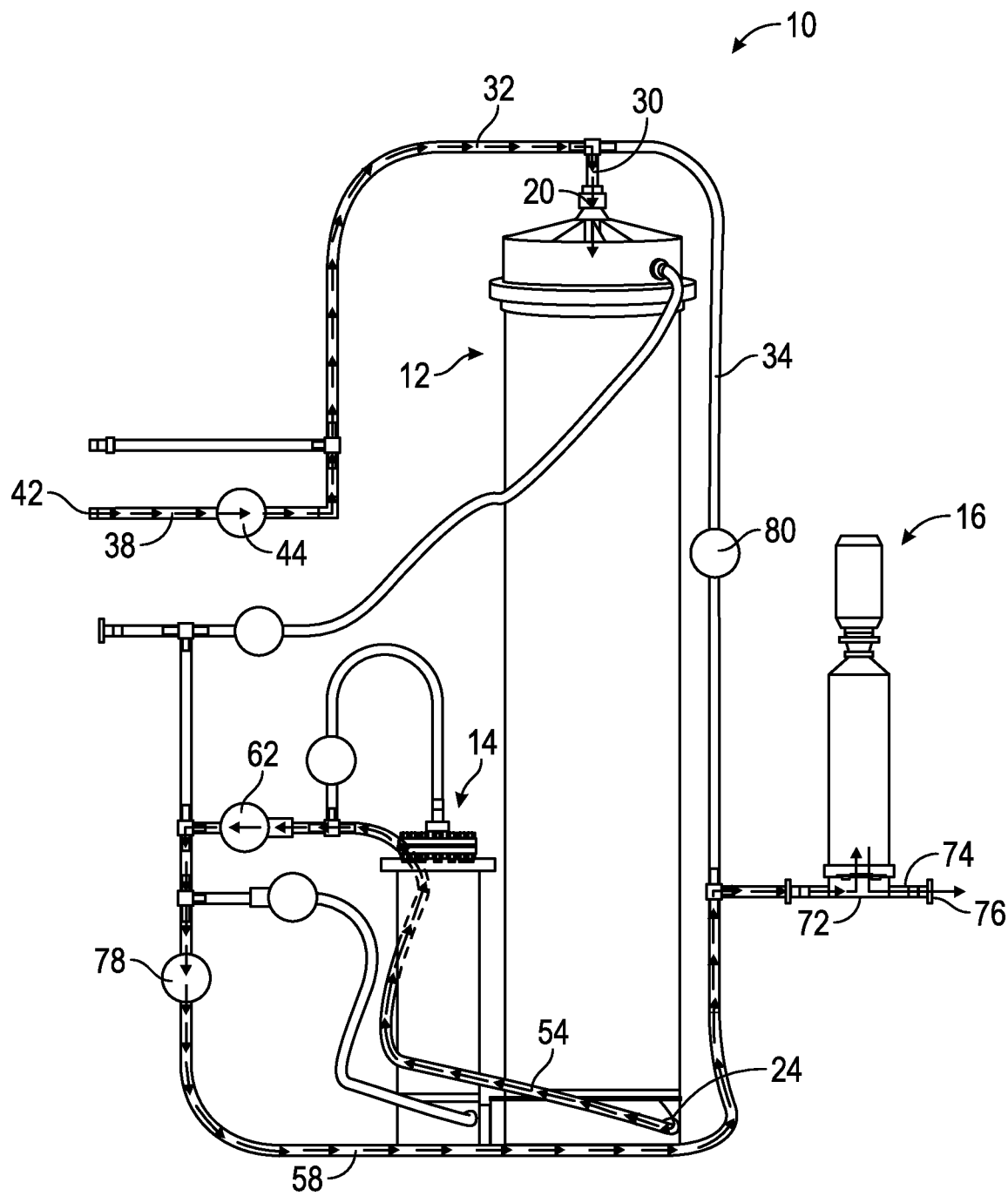

In addition to monitoring the pressure in the upper filter inlet tube 34 and the conductivity of the solution entering the filter 16, the mixing controller 100 further continuously monitors the volume of water consumed during the execution of the automated method 200 (e.g., by the volume sensor 94). Once a total predetermined volume of water is consumed, the mixing controller 100 closes the lower port valve 62, opens the second chamber inlet valve 70, and opens the second chamber outlet valve 68 (214). For example, in one embodiment, the mixing controller 100 closes the lower port valve 62, opens the second chamber inlet valve 70, and opens the second chamber outlet valve 68 once the total volume of water consumed is greater than or equal to 800 L. As shown in FIG. 4E, once this occurs, water flows from the water source through the water inlet tube 48 and into the second chamber tube 56. From the second chamber tube 56, the water flows into the second mixing chamber 14 via the second chamber lower port 66, where it mixes with the sodium bicarbonate powder in the second mixing chamber 14. Once the second mixing chamber 14 fills with water, the solution of water and bicarbonate is pushed out the second chamber top port 64 and into the second chamber outlet 60. The bicarbonate solution then flows from the second chamber outlet 60 into the lower flow tube 54, finally entering the first mixing chamber 12 by the lower port 24. Once the bicarbonate solution has entered the first mixing chamber 12, the bicarbonate solution mixes with the water and the powdered media contained therein. In this way, the sodium bicarbonate power (and/or any other additives contained within the second mixing chamber 14) is dissolved separately before being added to the solution in the first mixing chamber 12.

The mixing controller 100 keeps the valves in this configuration for a predetermined amount of time. After the predetermined amount of time has elapsed, the mixing controller 100 closes the second chamber inlet valve 70, closes the second chamber outlet valve 68, and opens the lower port valve 62 (216). For example, in one embodiment, the mixing controller 100 closes the second chamber inlet valve 70, closes the second chamber outlet valve 68, and opens the lower port valve 62 once at least five minutes have passed. This stops the water flow through the second mixing chamber 14 and reopens the water flow from the water source to the first mixing chamber 12 via the lower port 24, returning the mixing apparatus 10 to the configuration of steps 204 and 212 as shown in FIG. 4A.

Finally, once the mixing controller 100 determines (e.g., by the volume sensor 94) that the total volume of water consumed has reached a predetermined total volume, the mixing controller 100 closes the water source and the upper filter inlet valve 80. The mixing controller 100 further opens the compressed air valve 44 and the water bypass valve 78 (218). For example, in one embodiment, the mixing controller 100 closes the water source and the upper filter inlet valve 80 and opens the compressed air valve 44 and the water bypass valve 78 once 1,000 L of water has been consumed during the mixing process. Once this occurs, compressed air flows from the compressed air source into the compressed air inlet 38 by the compressed air entry 42. From the compressed air inlet 38, the compressed air flows into the common inlet 32 and into the first mixing chamber 12 by the top inlet/outlet 30 and via the top port 20. The compressed air flowing into the first mixing chamber 12 evacuates the solution remaining in the chamber 12 out of the chamber 12 through the lower port 24 and into the lower flow tube 54. The evacuated solution then flows through the lower flow tube 54, into the lower filter tube 58, and into the filter 16 by the filtration tubing section 72. After being filtered, the solution flows through the outlet 74 and into the collection vessel coupled to the apparatus exit 76. In this way, compressed air can be used to evacuate solution remaining in the first mixing chamber 12 out of the apparatus 10 and into the collection vessel, resulting in the collection vessel contents having the target volume yield (e.g., of 1,000 L of prepared liquid media).

Figure 4G:
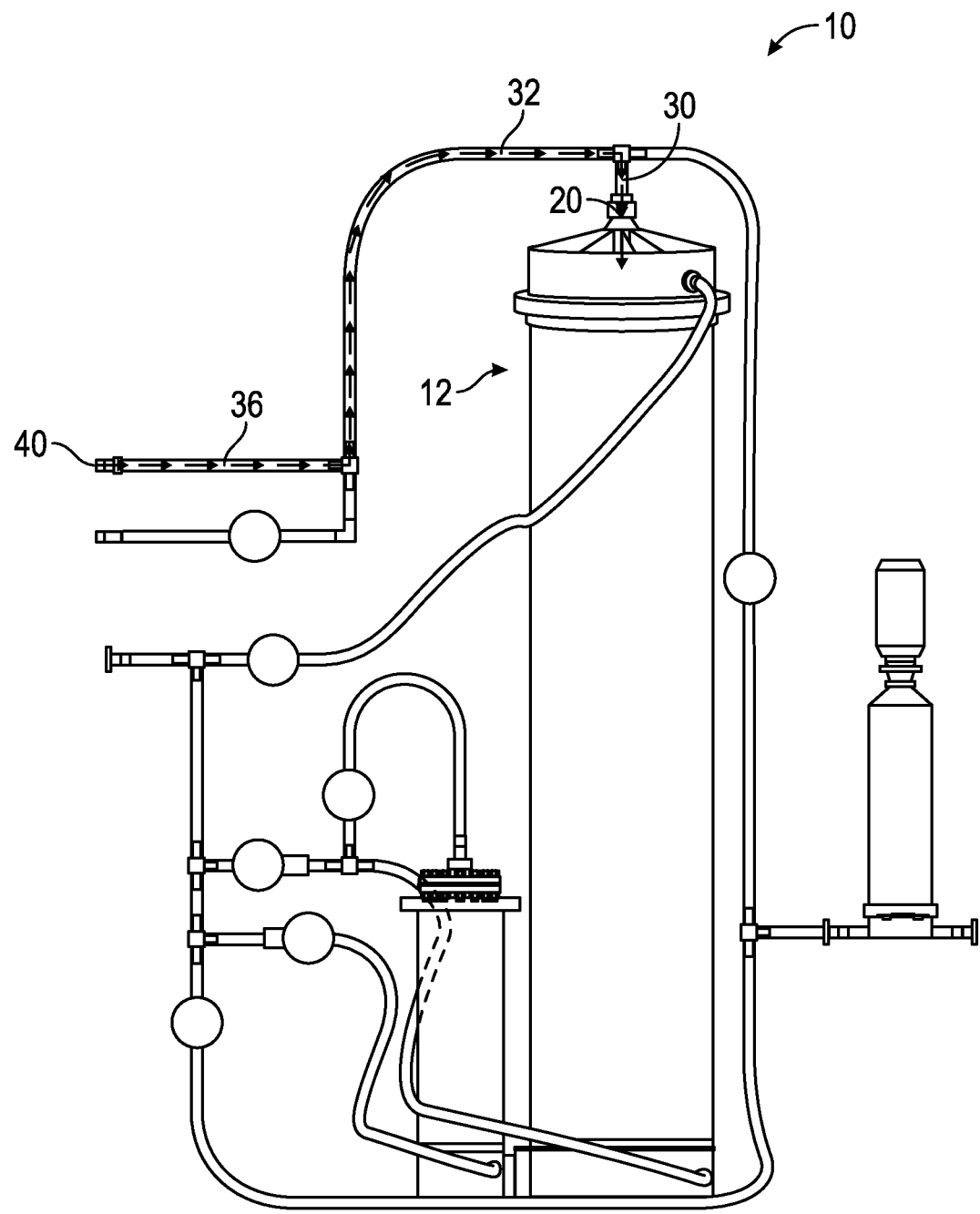

During any step of the automated method 200, a supplement may be added to the solution being mixed in the first mixing chamber 12. FIG. 4G illustrates the flow of a given supplement into the first mixing chamber 12. The supplement flows into the supplement inlet 36 of the apparatus 10 by the supplement entry 40 and follows the tubing of the supplement inlet 36 into common inlet 32. If the solution mixing in the first mixing chamber 12 is still contained in the chamber 12, the supplement flows from the common inlet 32 into the top inlet/outlet 30 and into the first mixing chamber 12 by the top port 20. If the solution mixing in the first mixing chamber 12 has filled the chamber 12 and is flowing out of the top port 20, the supplement mixes with the solution flowing out of the chamber 12 in the upper filter inlet tube 34.

However, while the above described automated method 200 is directed to the reconstitution of powdered cell culture media, it should be understood that embodiments of the mixing apparatus 10 may be used with automated method embodiments to reconstitute a variety of dry ingredients into liquids, such as a variety of bioprocess powders into bioprocess solutions. It is further contemplated that the liquid solvents employed can be water, alcohols, or other organics. The solubility characteristics, the solvent to be used, the amount required, and the chemical interactions between the solvent and the reconstituted chemicals will serve to provide guidelines for the embodiments of the automated method used to reconstitute the powders and the configuration of the mixing apparatus 10 used with a given automated method embodiment. Moreover, while the preferred embodiments described herein add liquids to dry ingredients for the purpose of reconstituting those dry ingredients, it is contemplated that the mixing apparatus can work equally well for the reconstitution of a concentrated liquid or a sequential combination of a liquid and a powder.

A variety of modified forms of the technology can be constructed for different end uses. For example, the mixing apparatus 10 may include only the first mixing chamber 12. Both the powdered media and the secondary additive, such as sodium bicarbonate, can be provided to the first mixing chamber 12 together. Therefore, only one chamber is needed to dissolve the solids in the fluids. As another example, the mixing apparatus 10 may include one or more additional mixing chambers aside from the first mixing chamber 12 and the second mixing chamber 14 (e.g., to separately mix additional secondary additives).

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the technology should not be taken to imply that the terminology is being redefined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged, or excluded from other embodiments.

The embodiments herein have been described with reference to drawings. The drawings illustrate certain details of specific embodiments that implement the systems and methods described herein. However, describing the embodiments with drawing should not be construed as imposing on the disclosure any limitations that may be present in the drawings.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims, are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but it not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be constructed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations.

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibility of including one of the terms, either of the terms, or both terms. For example, the phrase "A or B" will be understood to include the possibilities of "A" or "B" or "A and B."

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another, or with the two members or the two members and any additional intermediate members being attached to one another. Such joining may be permanent in nature or may be removable or releasable in nature.

The technology discussed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. An automated bioprocess solution preparation apparatus comprising:
    a first mixing chamber configured to contain at least one ingredient for a bioprocess solution, the first mixing chamber comprising a first port and a second port for a fluid to enter the mixing chamber and a third port for a liquid bioprocess solution prepared from the ingredients to exit the mixing chamber, the first port and the third port are located at a first end of the mixing chamber and the second port is located at a second end of the mixing chamber opposite the first end;
    an array of tubing for fluid flow within the apparatus;
    a sensor arranged to measure a property of the liquid bioprocess solution exiting the mixing chamber;
    a first valve associated with the first port; and
    a second valve associated with the second port,
    wherein, when the property meets or exceeds a threshold value, the apparatus is operable to perform at least one of the steps of:
        closing the first valve to block the fluid from entering the mixing chamber through the first port, and
        opening the second valve for the fluid to enter the mixing chamber through the second port.

2. The apparatus of claim 1, wherein the array of tubing comprises a fluid inlet tube coupled to a fluid source to receive water from the fluid source and coupled to the first valve such that the water flows from the fluid source through the first valve to the first port when the first valve is open.

3. The apparatus of claim 1, wherein the sensor comprises a pressure sensor, a conductivity sensor, a volume sensor, or a timer.

4. The apparatus of claim 1, further comprising a second mixing chamber containing an additive.

5. The apparatus of claim 4, wherein the second mixing chamber is connected by the array of tubing to the first port or the second port of the first mixing chamber.

6. The apparatus of claim 1, further comprising:
    a third valve associated with the third port, and
    a control system programmed to pulse an internal pressure of the first mixing chamber by closing and opening the third valve.

7. The apparatus of claim 1, wherein the at least one ingredient is a powdered dry ingredient or a granulated dry ingredient.

8. The apparatus of claim 1, further comprising a computing system configured to control the mixing apparatus, wherein the computing system is programmed to open the second valve from a fully closed position and fully close the first valve in response to the property meeting or exceeding the threshold value.

9. The apparatus of claim 8, wherein the computing system is further programmed to close the second valve in response to consumption of a predetermined total volume of water.

10. The apparatus of claim 9, wherein the computing system is further programed to open the second valve at a predetermined elapsed time following the close of the second valve.

11. The apparatus of claim 1, further comprising a filter coupled to the third port via the array of tubing.

12. The apparatus of claim 1, wherein the first port and the second port are oriented tangential to an inner wall of the first mixing chamber.

13. The apparatus of claim 12, wherein the third port is oriented perpendicular to the first port and the second port.

14. The apparatus of claim 12, further comprising a compressed air valve associated with the third port, wherein opening of the compressed air valve causes compressed air to flow toward the first mixing chamber.

15. An automated bioprocess solution preparation apparatus comprising:
a first mixing chamber configured to contain at least one ingredient for a bioprocess solution, the first mixing chamber comprising a first port and a second port for a fluid to enter the mixing chamber and a third port for a liquid bioprocess solution prepared from the ingredients to exit the mixing chamber;
an array of tubing for fluid flow within the apparatus;
a sensor arranged to measure a property of the liquid bioprocess solution exiting the mixing chamber;
a first valve associated with the first port;
a second valve associated with the second port;
a third valve associated with the third port; and
a control system programmed to pulse an internal pressure of the first mixing chamber by closing and opening the third valve,
wherein, when the property meets or exceeds a threshold value, the apparatus is operable to perform at least one of the steps of:
closing the first valve to block the fluid from entering the mixing chamber through the first port, and
opening the second valve for the fluid to enter the mixing chamber through the second port.

16. The apparatus of claim 15, wherein the first port and the third port are located at a first end of the mixing chamber and the second port is located at a second end of the mixing chamber.

17. An automated bioprocess solution preparation apparatus comprising:
a first mixing chamber configured to contain at least one ingredient for a bioprocess solution, the first mixing chamber comprising a first port and a second port for a fluid to enter the mixing chamber and a third port for a liquid bioprocess solution prepared from the ingredients to exit the mixing chamber;
an array of tubing for fluid flow within the apparatus;
a sensor arranged to measure a property of the liquid bioprocess solution exiting the mixing chamber;
a first valve associated with the first port;
a second valve associated with the second port; and
a computing system configured to control the mixing apparatus, wherein the computing system is programmed to, in response to the property meeting or exceeding a threshold value:
fully close the first valve to block the fluid from entering the mixing chamber through the first port; and
open the second valve from a fully closed position for the fluid to enter the mixing chamber through the second port.

18. The apparatus of claim 17, wherein the first port and the third port are located at a first end of the mixing chamber and the second port is located at a second end of the mixing chamber.

19. The apparatus of claim 17, further comprising a third valve associated with the third port, wherein the control system is programmed to pulse an internal pressure of the first mixing chamber by closing and opening the third valve.

20. The apparatus of claim 17, wherein the computing system is further programmed to close the second valve in response to consumption of a predetermined total volume of water and open the second valve at a predetermined elapsed time following the close of the second valve.

* * * * *